United States Patent
Goodwin

(10) Patent No.: US 8,070,705 B2
(45) Date of Patent: Dec. 6, 2011

(54) PROTECTIVE DEVICE USING A SPACER FABRIC

(75) Inventor: Edward L. Goodwin, Canton, MA (US)

(73) Assignee: HipSaver, Incorporated, Canton, MA (US)

(*) Notice: Subject to any disclaimer, the term of this patent is extended or adjusted under 35 U.S.C. 154(b) by 848 days.

(21) Appl. No.: 11/157,633

(22) Filed: Jun. 21, 2005

(65) Prior Publication Data
US 2006/0287622 A1 Dec. 21, 2006

(51) Int. Cl.
*A61F 13/00* (2006.01)
(52) U.S. Cl. .................. 602/60; 602/62; 602/63
(58) Field of Classification Search .............. 602/60–66, 602/75–79, 901, 904; 2/59, 115, 126, 120, 2/125; 66/195, 196
See application file for complete search history.

(56) References Cited

U.S. PATENT DOCUMENTS

| | | | | |
|---|---|---|---|---|
| 1,796,782 A * | 3/1931 | Gasperini | | 2/87 |
| 3,892,239 A * | 7/1975 | Masso Remiro | | 604/312 |
| 4,084,586 A * | 4/1978 | Hettick | | 602/60 |
| 4,294,240 A * | 10/1981 | Thill | | 602/21 |
| 5,020,164 A * | 6/1991 | Edwards | | 2/239 |
| 5,651,847 A * | 7/1997 | Loeffler | | 66/19 |
| 5,735,807 A * | 4/1998 | Cropper | | 602/63 |
| 6,110,135 A * | 8/2000 | Madow et al. | | 602/20 |
| 6,378,139 B1 * | 4/2002 | Mazzaglia | | 2/242 |
| 6,499,320 B1 * | 12/2002 | Bernhardt | | 66/178 R |
| 6,627,562 B1 * | 9/2003 | Gehring, Jr. | | 442/35 |
| 6,978,643 B2 * | 12/2005 | Akers et al. | | 66/170 |
| 7,080,412 B2 * | 7/2006 | Zeiler | | 2/4 |
| 7,090,651 B2 * | 8/2006 | Chiang et al. | | 602/5 |
| 7,268,269 B2 * | 9/2007 | Axtell et al. | | 588/299 |
| 7,276,275 B2 * | 10/2007 | Schindzielorz et al. | | 428/86 |
| 2002/0146536 A1 * | 10/2002 | Bard | | 428/138 |
| 2004/0003630 A1 * | 1/2004 | Akers et al. | | 66/197 |

* cited by examiner

*Primary Examiner* — Michael A. Brown
(74) *Attorney, Agent, or Firm* — Clark & Elbing LLP

(57) ABSTRACT

A protective sleeve for a body extremity, such as an arm or a leg. The sleeve includes a spacer textile formed into a self-supporting tube for protecting the extremity from pressure, friction, shear, skin tears and bruising. The tube can have a wide end and a narrow end. The extremity slides through the wide end of the tube and the narrow tube end then slides over the foot or hand. Because these tubes are self-supporting, the sleeve can remain coextensive with the extremity while maintaining a loose fit, even during vigorous exercise. The spacer textile provides for both pressure relief and moisture transmission from the skin.

10 Claims, 3 Drawing Sheets

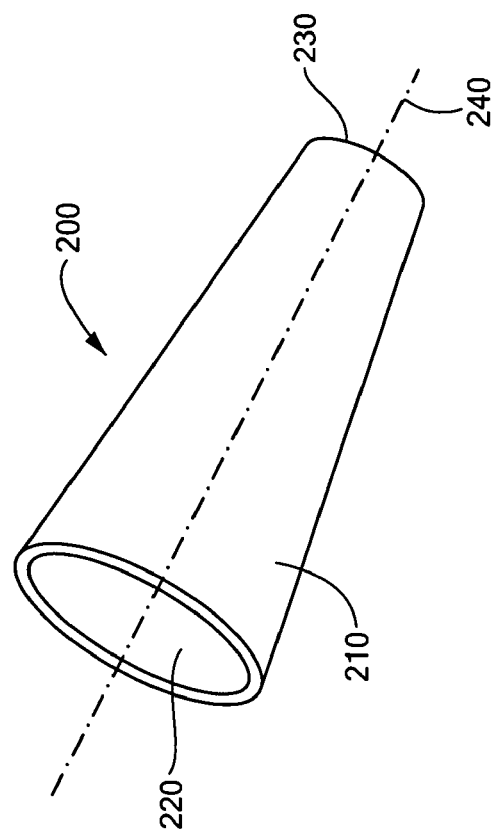
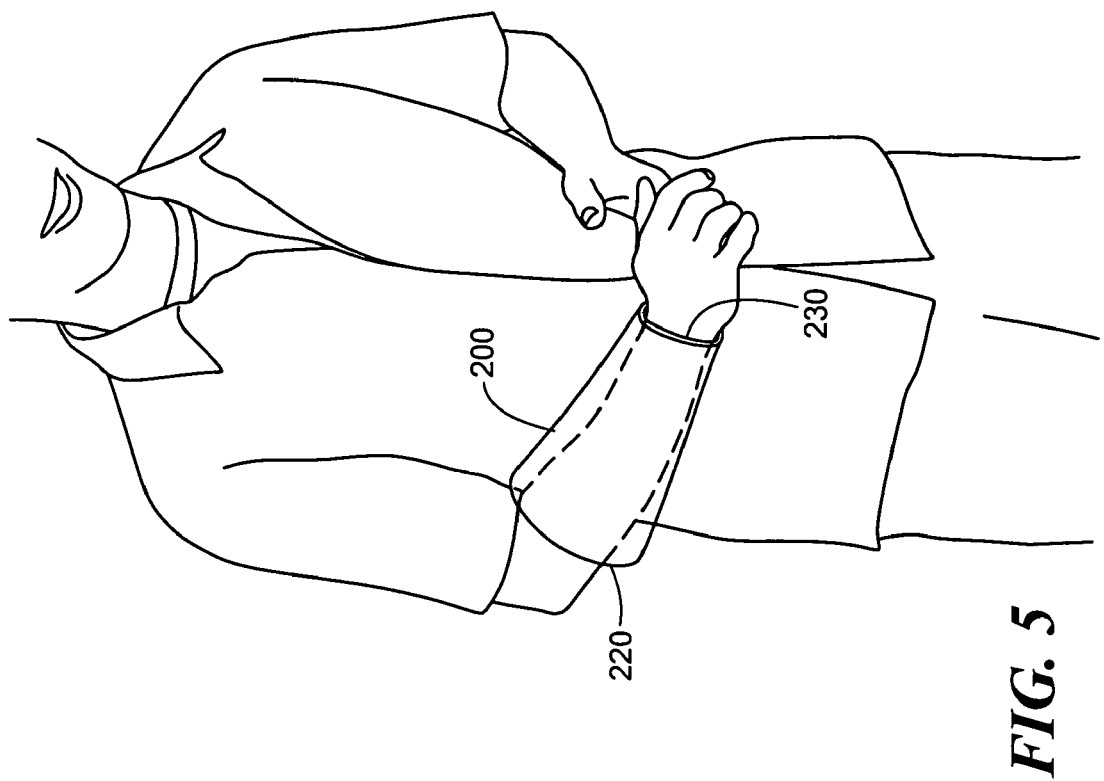
FIG. 4
FIG. 5

PROTECTIVE DEVICE USING A SPACER FABRIC

TECHNICAL FIELD

The present invention relates to protective devices that may be worn to guard against injuries from impact or pressure.

BACKGROUND

People at risk for compromised skin integrity must take special measures to protect the skin surface. The infirm, the elderly, burn victims, athletes, and some occupational workers fall into this category. For example, pressure sores (such as decubitis ulcers, bed sores, etc.) are a major problem for the immobile, infirm population. Major factors leading to skin injury, such as sores, cut and abrasions include pressure or impact, friction, shear force, and moisture trapped against the skin. Conventional support surfaces can mitigate some, but not all, of these factors. In particular, many support surfaces relieve pressure but trap moisture against the skin. The moisture trapped between the skin and surfaces such as neoprene foam, gels, inflatables, etc. acts to irritate the skin and accelerate pressure related injury, such as sore development. Therefore, pressure relieving surfaces that allow for moisture escape would be valuable in the prevention and treatment of skin injury.

SUMMARY OF THE INVENTION

In a first embodiment of the invention, a layered spacer textile fabric is provided. Each layer includes two fabric substrates joined by an array of filaments where the filaments run perpendicular to each substrate. In some embodiments the natural bowing of the filaments run in the same direction for the layers, while in other embodiments the bowing or orientation of the layers is staggered.

In another embodiment of the invention, a protective sleeve of spacer textile fabric is provided. The spacer textile is formed into a tube with a wider opening at one end and a narrower opening at the other end. An extremity such as an arm or a leg slides through the wide end of the tube and then the end of the extremity slides through the narrow end of the tube. The diameter of the narrow end of the tube is set so that the tube rests on the end of the hand or foot that is proximate to the body trunk. The stiffness of the spacer textile allows the tube to stand on end, resting on the hand or foot. The sleeve diameter may be set so that the sleeve is a loose fit on the extremity, but will remain in place, coextensive with the extremity, even during vigorous activity. The permeability to moisture of the spacer textile and the loose fit of the sleeve allows for air circulation and permits moisture to escape. The natural resilience of the spacer textile can protect the skin from pressure, sheer forces, and friction.

BRIEF DESCRIPTION OF THE DRAWINGS

The foregoing features of the invention will be more readily understood by reference to the following detailed description, taken with reference to the accompanying drawings, in which:

FIG. 4 is a protective sleeve for a body extremity according to an embodiment of the invention; and FIG. 5 shows the protective sleeve of the embodiment of FIG. 4 positioned on a human arm.

DETAILED DESCRIPTION OF SPECIFIC EMBODIMENTS

Definitions. As used in this description and the accompanying claims, the following terms shall have the meanings indicated, unless the context otherwise requires:

A "spacer textile" means any fabric comprising two textile substrates joined together by an array of filaments where the filaments are substantially perpendicular to the substrates.

The "orientation" of a spacer textile means a direction, parallel to the substrate, towards which a majority of the filaments bow, when the textile is compressed perpendicular to the substrate.

A "tube" shall mean a generally cylindrical object with an opening at each end where the diameter of the cylinder can vary along the longitudinal axis of the cylinder.

A tube is "self supporting" if the tube can stand on at least one end without collapsing along the longitudinal axis of the tube.

Figure 1:
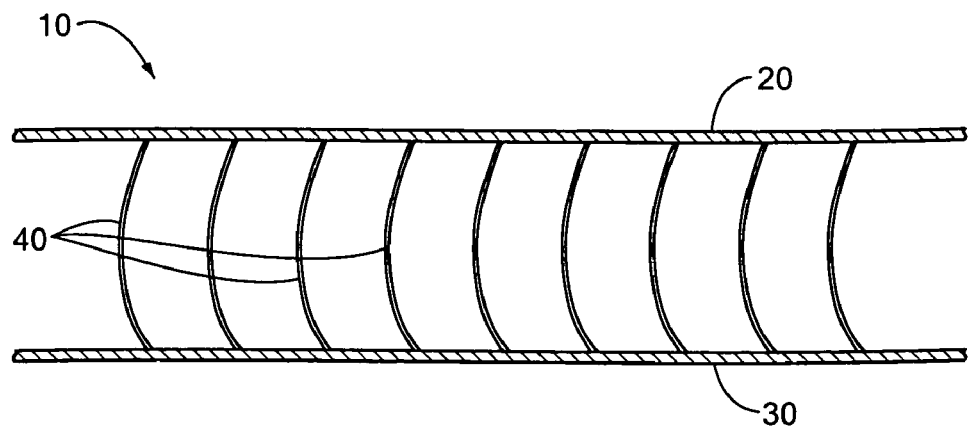
FIG. 1 is a side view of a spacer textile.
Figure 2:
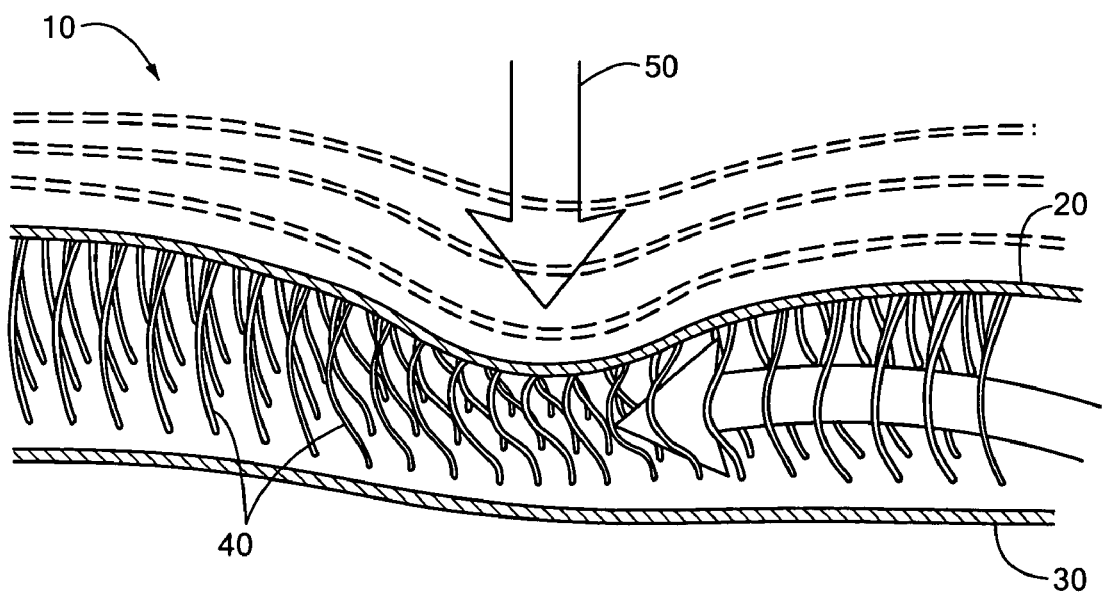
FIG. 2 is a perspective view of a spacer textile subjected to a force normal to the face of the textile.

Spacer textiles, which are also called three dimensional textiles, hold promise for applications that require relief from pressure, friction, shear force, or moisture trapped against the skin. As shown in FIG. 1, a spacer textile 10 consists of two fabric substrates 20, 30, which may be knit fabrics, connected by filaments 40, which may be monofilaments, that are substantially perpendicular to the two fabric substrates. When subjected to a force 50, as shown in FIG. 2, these textiles are resilient due to the connecting filaments that act like miniature springs. Thus, spacer textiles may be used for pressure relief and to mitigate shear forces and friction applied to the textile surface. Most importantly, these spacer textile fabrics have spaces between the filaments, allowing moisture to move freely through the fabric. Note in FIG. 2 the uniformly oriented, slightly bowed structure of the filaments 40 connecting the substrates, which is typical of spacer textiles. The structure results in a tendency to deflect unevenly when depressed, creating unbalanced pressure relieving forces. The orientation or bow of a spacer fabric corresponds to the direction in which these filaments deflect.

Figure 3:
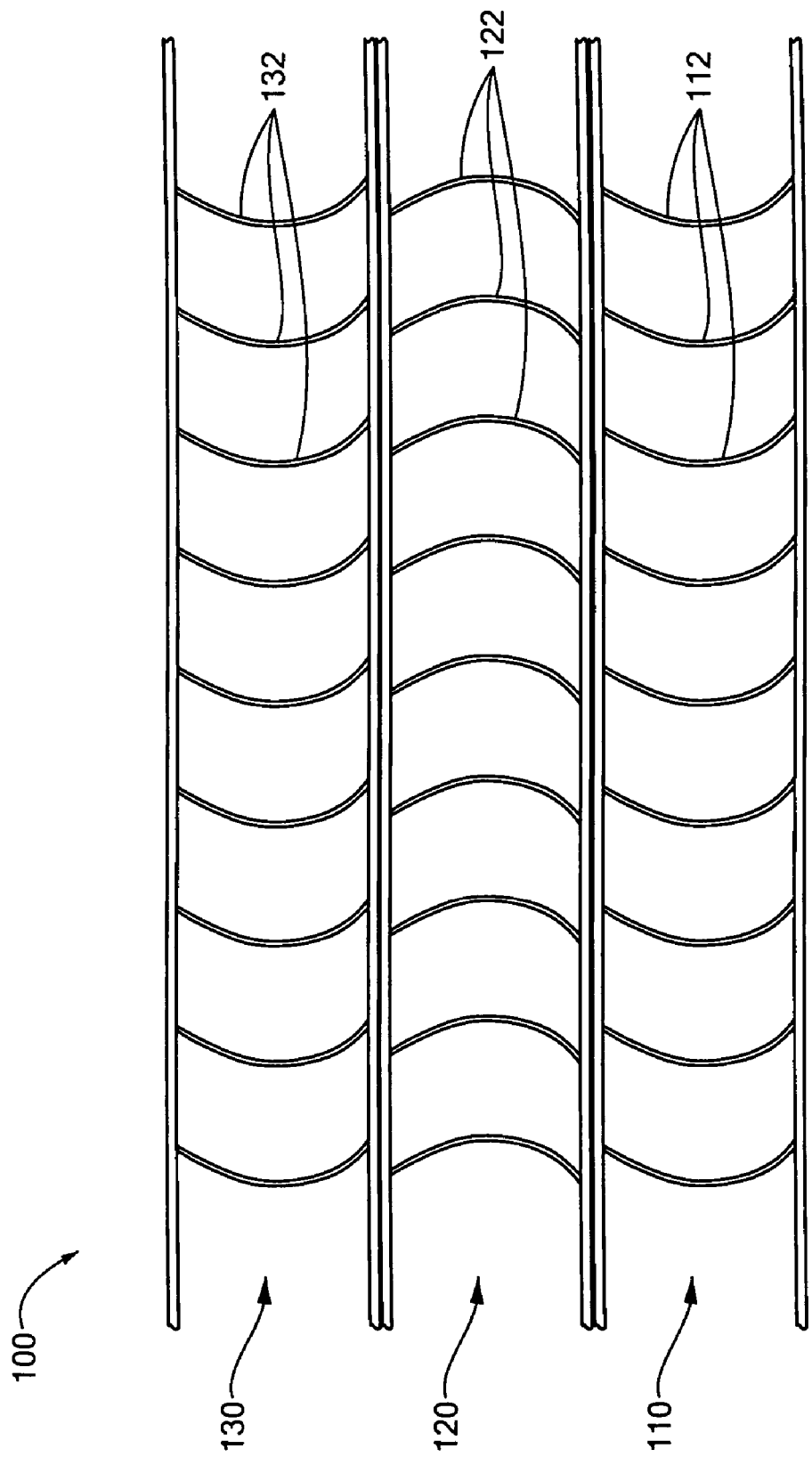
FIG. 3 shows a layered spacer textile according to an embodiment of the invention.

While a single layer of spacer fabric may be employed in many applications, in a first embodiment of the invention, a layered spacer fabric 100 is fabricated with two or more layers of a spacer textile, as shown in FIG. 3. The fabric of FIG. 3 includes three layers 110, 120, 130, but any number of layers may be included. The layered fabric of FIG. 3 has the advantage of functioning more smoothly and finely to resist pressure at the thickness necessary for a pressure relieving surface (generally about half an inch), when compared to a fabric consisting of a single layer of spacer textile. Further, a multilayer construction of thinner spacer textiles offers the additional advantage of being more compatible with sewing as a fabrication technique than a single layer fabric.

In another embodiment of the invention, the filament bow orientation of the layers of the spacer fabric is staggered. For example, as shown in FIG. 3, the bow orientation between adjacent layers may be set so that orientation of the filaments 112, 122, 132 in adjacent layers differs by 180 degrees. Such fabrics will demonstrate an interface pressure reduction when compared to fabrics with a single layer or layers oriented in the same direction. In specific embodiments of the invention, the orientation of adjacent layers may differ by any amount between 0 degrees and 180 degrees. Staggering the orientation of the layers advantageously reduces the directionality of the pressure absorbing properties of the spacer textile.

In another embodiment of the present invention, a protective sleeve 200 is provided for a body part or extremity, such as an arm or a leg. As shown in FIG. 4, the sleeve comprises a spacer 210 textile formed into a tube. The tube has openings on each end 220, 230 and can vary in diameter along its longitudinal axis 240. The tube can be self-supporting due to the structure of the spacer textile, i.e., the tube can stand on end. When one end of the tube is made smaller than the other tube end, an arm or leg may be first slipped through the wider tube 220 end and a hand or an ankle may then be slipped through the narrower tube end 230. The natural resilience of the spacer textile fabric allows the narrower tube end to stretch to allow passage of the hand or foot through the opening and the tube end then resumes its normal diameter. The diameter of the narrow end may be set so that the tube end rests on the end of the hand or foot that is proximate to the body trunk, as shown in FIG. 5. Because the spacer textile tube is supported at its base by resting on a hand or foot, it is possible to have the entire structure remain loose around the extremity, while the sleeve remains coextensive with the extremity, even during vigorous exercise. The spacer textile in the sleeve provides both for pressure relief due to its resilience and for moisture transmission. The loose-fitting nature of the sleeve advantageously allows for air access to the skin.

In various embodiments of the invention, the tube ends may be of the same diameter while in other embodiments, the diameter of the narrower end of the tube may be only a fraction of the diameter of the wider end of the tube, such as 0.8.

In some embodiments of the invention, elastomeric material or a resilient stretch knit material is incorporated into the narrower tube end to ensure that the narrower end of the tube makes a suitably snug fit to the ankle or wrist, after the tube end has been pulled over the foot or hand. In alternative embodiments of the invention, a fastener may be provided at one end of the tube to provide the restricted tube diameter necessary so that the tube end rests on the hand or foot end that is proximate to the body trunk. The fastener may be unfastened when the extremity is inserted into the sleeve and then fastened so that the end of the sleeve is retained on the extremity in the correct position. The fastener may be any fastener known in the art, including a hook and loop fastener, such as Velcro™, a snap, a button and button hole, etc. Alternatively or in addition, the end of the tube may include a stirrup, a glove or a sock to retain the end of the tube at the appropriate position on the extremity. The term "glove" or "sock" as used in this specification and in any appended claims shall include a partial glove or a partial sock that covers only a portion of a hand or foot, as well as a full glove or sock. For example, a glove may cover only a thumb or a part of a thumb or any combination of thumb and figures.

In some embodiments of the invention, the tube of the protective sleeve may be formed by a unitary knitting operation. Alternatively, the spacer textile may be formed as a sheet and then fashioned into a tube by seaming together edges of the sheet. This seam may be formed by sewing or any bonding process known in the art, such as gluing, thermal bonding, etc. The edges of the spacer textile may be joined by a fastener, such as Velcro™, a button and button hole, a hook and loop, a strap, etc.

In some embodiments of the invention, the spacer textile in the protective sleeve is a single layer fabric. In other embodiments, the spacer textile is formed in two or more layers, with the same orientation or any combination of differing orientations. In a specific embodiment, the orientation of adjacent layers is staggered by 180 degrees.

In some preferred embodiments of the invention, the tube in the protective sleeve includes one or more openings in addition to the tube end openings. These openings may provide convenient access to the skin of the protected extremity. In other embodiments, the tube may include one or more pockets. Any pocket or combination of pockets may be formed on the inside or outside of the tube. The pockets may, for example, hold a medical sensor or infusion device, etc.

In some embodiments of the invention, the protective sleeve may include additional material affixed to the tube of spacer textile. For instance, the tube may have an outer layer of more pressure resistant material, such as a fiberglass. In preferred embodiments, certain portions of the tube may include additional material to provide greater pressure resilience. For example, a portion of the tube that is positioned at an elbow or knee may include additional layers of spacer textile to increase pressure resilience. Alternatively, portions of the tube may include foam such as neoprene foam, either on the inside or outside tube surface.

A loose fitting protective sleeve, such as any of the embodiments of the invention, could be used to cover an intravenous connection site or itchy wound site. In other applications, the sleeve could replace bandages and tapes to cover and medicate wounds or burns. The loose fitting nature of the protective sleeves allows for ease of application and removal. In particular, more frequent inspection of skin and wound sites is facilitated.

In another embodiment of the invention, an elbow or heel protector may be formed from a spacer fabric. The spacer fabric may be a multi-layered fabric with the bow orientation of the spacer fabric layers aligned among the layers or, preferably, staggered among the layers. The elbow or heel protector may be made generally from a tube of spacer fabric with a bend formed by sewing, thermoforming, fusing or any other technique known in the art.

Similarly, it is of course apparent that the present invention is not limited to the detailed description set forth above. Various changes and modifications of this invention as described will be apparent to those skilled in the art without departing from the spirit and scope of this invention as defined in the appended claims.

What is claimed is:

1. A loose-fitting, self-supporting protective sleeve for a body part, the sleeve comprising a plurality of layers of spacer textile formed into a tube.

2. A protective sleeve according to claim 1 wherein the tube ends are of different diameters.

3. A protective sleeve according to claim 1 wherein the diameter of the tube at one end is less than 80% of the diameter of the tube at the other end.

4. A protective sleeve according to claim 1 wherein the tube includes elastomeric material at one end of the tube.

5. A protective sleeve according to claim 1 wherein the tube includes a resilient stretch knit at one end of the tube.

6. A protective sleeve according to claim 1 wherein the tube is entirely formed by a knitting process.

7. A method for protecting a body part with a loose-fitting, self supporting protective sleeve, the body part appended to a body trunk and characterized by an end proximate to the trunk and an end distal to the trunk, the method comprising: providing a loose-fitting, self supporting protective sleeve, the sleeve comprising a spacer textile formed into a tube, a second end of the tube smaller than a first end of the tube; and sliding the distal end of the body part through the first tube end and then sliding the distal end of the body part through the second tube end, the second end sized to assist in retaining the sleeve in position with respect to the body part.

8. A method according to claim 7 wherein the spacer textile includes a plurality of layers.

9. A self-supporting protective sleeve for a body part, the sleeve comprising a first end, a second end, and a central tube, wherein the central tube consists of spacer textile and a seam formed by sewing.

10. A method for protecting a body part with a loose-fitting, self supporting protective sleeve, the body part appended to a body trunk and characterized by an end proximate to the trunk and an end distal to the trunk, the method comprising:

(a) providing a protective sleeve, the sleeve comprising a first end, a second end, and a central tube, wherein the central tube consists of spacer textile and a seam formed by sewing, and the second end of the tube is smaller than the first end of the tube; and (b) sliding the distal end of the body part through the first tube end and then sliding the distal end of the body part through the second tube end, the second end sized to assist in retaining the sleeve in position with respect to the body part.

* * * * *